United States Patent [19]

Starkey et al.

[11] Patent Number: 5,137,288
[45] Date of Patent: Aug. 11, 1992

[54] SIDE LOADING WIRE GRIP

[75] Inventors: John J. Starkey, Cooper City; Fernando M. Viera, Hialeah; Matthew A. Palmer, Miami, all of Fla.

[73] Assignee: Cordis Corporation, Miami Lakes, Fla.

[21] Appl. No.: 733,218

[22] Filed: Jul. 22, 1991

[51] Int. Cl.⁵ ............................................. A61B 17/00
[52] U.S. Cl. ..................................... 279/42; 279/48; 604/159; 604/171
[58] Field of Search ............. 279/41 R, 42, 48, 46 R, 279/43.1, 43.2, 43.4, 46.2, 46.3; 24/136 R, 136 B, 115 M; 254/134.3 R, 134.3 FT; 16/114 B; 604/159, 171, 178; 226/127

[56] References Cited

U.S. PATENT DOCUMENTS

| 4,210,863 | 7/1980 | Hunt et al. ........................ 279/42 X |
| 4,784,612 | 11/1988 | Ryan ................................. 439/369 X |
| 4,858,810 | 8/1989 | Intlekofer et al. ............ 24/115 M X |

Primary Examiner—Steven C. Bishop
Attorney, Agent, or Firm—Gerstman & Ellis

[57] ABSTRACT

A wire gripping handle for attaching to and detaching from wires defines a first tubular member, and a second tubular member which receives the first tubular member in generally coaxial relation. Both tubular members define a longitudinal slot so that, when the slots are aligned, a wire may be placed into the bores of the joined tubular members in lateral fashion. Then, upon relative rotation of the tubular members, a portion of one of them may be radially collapsed into gripping relation with the wire.

12 Claims, 1 Drawing Sheet

5,137,288

SIDE LOADING WIRE GRIP

BACKGROUND OF THE INVENTION

Guidewires are used for the insertion of catheters into the arterial system of a patient. After insertion of the guidewire to the proper location, the catheter is threaded over the guidewire and assisted in its advance to the proper site by following the guidewire.

As the guidewire is advanced, typically in a guiding catheter, the surgeon needs to rotate the guidewire to facilitate its advancement through the branching arterial pathways.

Because it is often difficult to rotate a small-diameter guidewire, a pin vise has been used in the prior art to serve as a rotating handle for the guidewire. A pin vise is a well-known item which comprises a structure like a small drill chuck with a cylindrical handle. The chuck is threaded over the proximal end of the guidewire and advanced to a desired position. A chuck collet, a part of the pin vise, may be then tightened onto the wire so that the pin vise is firmly attached to the guidewire, and serves as a rotating handle to facilitate the manual rotating of the guidewire as it is advanced.

It has been a disadvantage of conventional guidewire rotating handles that they must be applied to the guidewire from the end. By this invention, a side loading wire grip is provided which may serve as a handle for rotating a guidewire, and which may be laterally applied to the guidewire at any desired position. Its attachment is very quick, so that the surgeon may apply the wire grip of this invention to an intermediate position on the guidewire spaced from the ends; advance the guidewire a certain amount; loosen the wire grip of this invention and shift it proximally along the guidewire a certain degree; followed by once again further advancing the guidewire. By this means, the side loading wire grip may be quickly applied along any position of the guidewire rather than having to find the proximal end, to slide it from the end to the intermediate position along the guidewire where its use is desired.

DESCRIPTION OF THE INVENTION

In this invention a wire-gripping handle is provided for attaching to and detaching from wires. The handle comprises a first tubular member having a first bore, and a first side wall which defines a first longitudinal slot extending across at least one end of the first tubular member and preferably along its entire length. This permits a wire to be laterally inserted through the slot to occupy at least part and preferably the entire length of the first bore, and to extend from the first bore longitudinally out of the one end.

A second tubular member is provided, having a second bore which receives a portion of the first tubular member, including the one end. Thus, a wire extending out of the one end also can extend through the second bore out of the end of the second tubular member which faces away from the first tubular member. The second tubular member has a second side wall that defines a second longitudinal, wire-passing slot extending between its ends.

Threaded means are provided to permit the first and second tubular members to be rotatably advanceable and retractable relative to each other. The second bore is proportioned to radially collapse a portion of the first tubular member adjacent the one end as the first and second members are rotatably advanced relative to each other, to grip a wire carried therein.

The wire gripping handle of this invention preferably has a one end of the first tubular member which defines a plurality of radial slots. This facilitates the radial collapse thereof by the bore of the second tubular member as the two tubular members are advanced in screw threaded relation together. Also, the one end of the first tubular member defines at least portions of a substantially conical surface which, in turn, defines at least portions of the radial slots described above.

The second tubular member also preferably defines a substantially conical step in its second bore adjacent the facing-away end of the second tubular member, to fittingly engage the substantially conical surface of the first tubular member. Thus, pressurization between the surface and the step can cause the radial collapse described above, which radial collapse results in gripping of the wire by the wire-gripping handle.

Typically, the portion of the first tubular member which is adjacent the one end has an outer diameter that is less than other portions of the tubular member. Likewise, the bore portion of the second tubular member adjacent the one end has an inner diameter that is less than the other portions of the inner diameter of said second tubular member.

DESCRIPTION OF THE DRAWINGS

In the drawings.

FIG. 4 is a sectional view taken along line 4—4 of FIG. 2a.

DESCRIPTION OF SPECIFIC EMBODIMENTS

Figure 1:
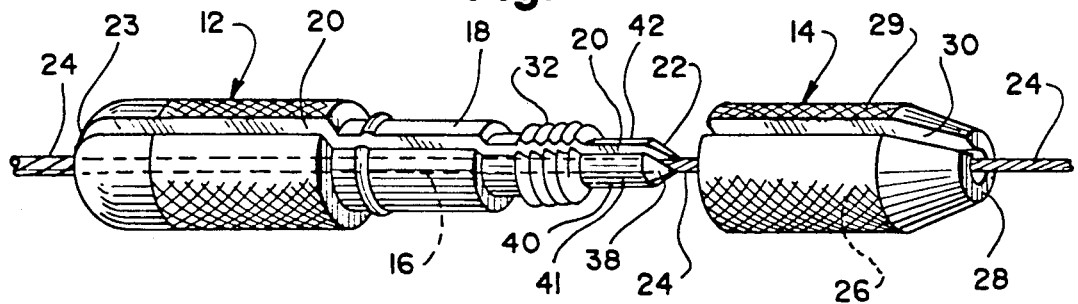
FIG. 1 is a perspective view of one embodiment of the wire-gripping handle of this invention, with the first and second tubular members being separated, and with a wire extending through the bores of both.
Figure 2:
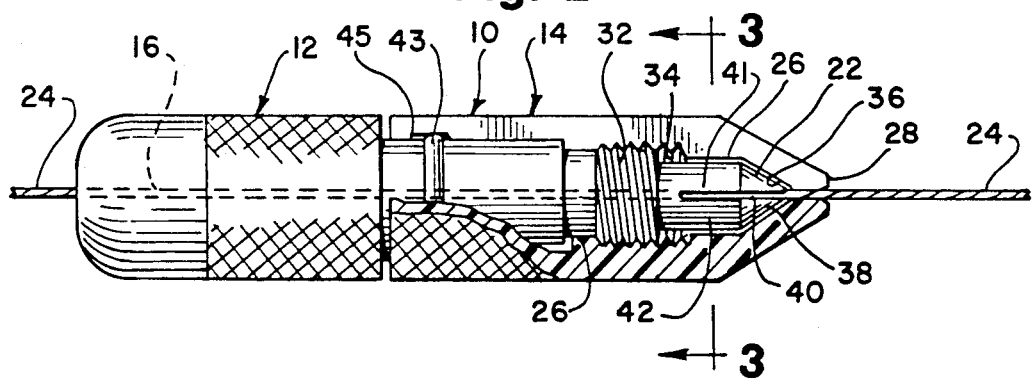
FIG. 2 is an elevational view of the wire gripping handle of FIG. 1, shown in assembled condition and taken partly in section, prior to moving into wire-gripping configuration.

Referring to the drawings, the wire gripping handle 10 of this invention is disclosed, comprising a pair of molded plastic tubular members 12, 14. First tubular member 12 defines a first bore 16 extending through the entire length of first tubular member 12, with the first bore being surrounded by a side wall 18 of molded, substantially rigid plastic. Longitudinal slot 20 extends through the side wall into first bore 16, and preferably extends across at least both ends 22, 23 of first tubular member 12, and along the entire length thereof. Thus, a wire 24, such as a guidewire for a catheter, may be laterally inserted through slot 20 so that wire 24 can occupy the bore or lumen of first tubular member 12, to extend from first bore 16 longitudinally out of both ends of member 12, as shown in FIGS. 1 and 2.

Second tubular member 14 defines a second bore 26. As shown in FIG. 2, the second bore 26 receives a portion of first tubular member 12 including end 22 thereof. Thus, wire 24 extending out of end 22 can also extend from the distal end 28 of second tubular member 14, distal end 28 being the end of second tubular member 14 which faces away from first tubular member 12.

Second tubular member 14 defines a sidewall 29 which, in turn, defines a second longitudinal slot 30 extending completely along the length thereof, which slot is proportioned to allow the passage of wire 24 through it from the exterior into the bore 26.

Figure 3:
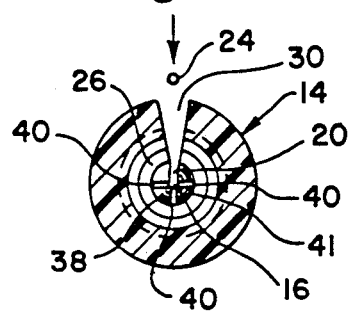
FIG. 3 is a sectional view taken along line 3—3 of FIG. 2.

Thus, it can be seen that both first and second tubular members 12, 14 can be mounted onto a cable or wire 24 at a point intermediate the ends by simply passing the cable 24 through the respective, aligned slots 20, 30 as shown in FIG. 3.

Accordingly, there is no need to engage in the time consuming process of threading tubular members 12, 14 onto the wire 24 from an end thereof.

First tubular member 12 defines external threads 32, which are proportioned to be engagable with internal threads 34 of second tubular member 14, defined in bore 26 thereof. Thus, as shown in FIG. 2, the respective tubular members 12, 14 can be brought into threaded engagement with each other to be advanceable and retractable relative to each other as they rotate.

Second bore 26 defines a conical shoulder 36, typically having an angle on the order of 31° to the longitudinal axis of tubular members 12, 14 and also wire 24. Correspondingly, first tubular member 12 defines a conical surface 38, typically of equal angle to shoulder 36, at its distal end through which first slot 20 extends. Conical surface 38 is proportioned to impinge against conical surface 36 as tubular members 12, 14 are advanced together in screw threaded relation.

Conical surface 38 also defines a plurality of slots 40 radiating from the apex of conical surface 38, where slot 20 communicates at its end with the exterior, with slots 40 extending rearwardly along a cylindrical portion 42 of first tubular member 12. Thus, at least a portion of tubular member 42 defines a series of longitudinally extending finger portions 41 defined between the respective slots 40 which extend part way along first tubular member 12, and slot 20 which extends completely along the length of member 12.

Figure 2A:
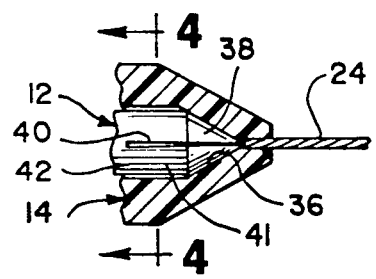
FIG. 2a is a longitudinal sectional view of a portion of the wire-gripping handle as shown in FIG. 2 in a fully advanced configuration wherein the wire is being firmly gripped.

Accordingly, as shown in FIG. 2a when conical surface 38 is driven into conical shoulder 36 by the screw threaded advancement of the respective tubular members 12, 14, the finger portions of section 42 and conical surface 38 are driven radially inwardly from their natural, unstressed configuration as shown in FIG. 2, to clamp against and retain any wire 24 that may be occupying the wire gripping handle. Then, to release the handle, one simply unscrews members 12, 14 a certain distance, to cause the fingers defined by cylindrical section 42 to be released toward their natural, unstressed configuration.

Detent ring 43 of member 12 fits in removable, snap-fit relation with annular slot 45. Thus, at a certain point in the process of unscrewing members 12 and 14, the surgeon feels a resistance as ring 43 is being rearwardly pushed out of slot 45. This serves as a warning that members 12, 14 are about to disconnect from their threaded relation.

Figure 4:
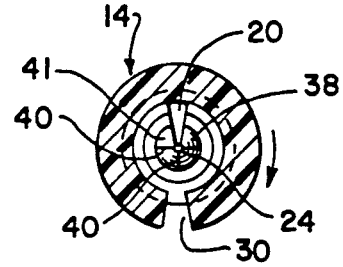

As shown in FIG. 3, a wire 24 may be placed into the respective bores 16, 26 by rotating the respective tubular members 12, 14 until their longitudinal slots 20, 30 align. As indicated by the arrow, wire 24 may then be placed into the wire gripping handle. Following this, as shown in FIG. 4, the members 12, 14 of the handle may be relatively rotated so that slots 20, 30 no longer align. At the same time, members 12, 14 are advanced together to cause the radial collapse of the fingers 41 of section 42, 38 as illustrated in FIG. 2a, so that handle 10 is firmly secured to wire 24. As this takes place, slots 40 are collapsed as shown in FIGS. 2a and 4, providing room for the radially inward collapse of the fingers 41 into gripping relation with wire 24.

Accordingly, when handle 10 is carried in gripping relation on a wire 24 as illustrated in FIGS. 2a and 4, the user is provided with a reliable means for applying torque to a guidewire 24 or any other desired wire for use in any manner. Handle 10 is easily applied at any point along the length of a wire by side mounting, and it is easily removed simply by screwing the respective tubular members 12, 14 apart into a rotary position where the slots 20, 30 are aligned. Then the handle 10 can simply laterally fall off of the wire. Thus, the handle of this invention can be applied, used, and removed at great speed during any desired surgical or other procedure involving a wire that needs to be rotated or otherwise manipulated.

The above has been offered for illustrative purposes only, and is not intended to limit the scope of the invention of this application, which is as defined in the claims below.

That which is claimed is:

1. A wire-gripping handle for attaching to and detaching from catheter guidewires and the like, which handle comprises:

a first tubular member having a first bore, and a first side wall which defines a longitudinal slot extending across at least one end of said first tubular member, to permit a wire to be laterally inserted through said slot to occupy at least part of said first bore and to extend from said first bore longitudinally out of said one end;

a second tubular member having a second bore which receives a portion of said first tubular member including said one end, whereby a wire extending out of said one end also can extend from said second bore out of the end of said second tubular member which faces away from said first tubular member;

said second tubular member having a second side wall that defines a longitudinal, wire-passing slot extending between its ends;

threaded means to permit said first and second tubular members to be rotatably advanceable and retractable relative to each other, the first tubular member and second bore being proportioned to radially collapse a portion of said first tubular member adjacent said one end as the first and second members are rotatably advanced relative to each other, to grip a wire carried therein.

2. The wire-gripping handle of claim 1 in which said slot of the first tubular member extends along the entire length of said first tubular member.

3. The wire-gripping handle of claim 1 in which the portion adjacent said one end of said first tubular member defines a plurality of radial slots to facilitate the radial collapse thereof.

4. The wire-gripping handle of claim 3 in which the one end of said first tubular member defines a substantially conical surface which, in turn, defines said radial slots, said second tubular member defining a substantially conical step in the second bore adjacent the facing-away end of said second tubular member, to fittingly engage said substantially conical surface, whereby pressurization between said surface and said step can cause said radial collapse.

5. The wire gripping handle of claim 1 in which the portion of the first tubular member adjacent said one end has an outer diameter that is less than other portions of said first tubular member.

6. The wire gripping handle of claim 5 in which the second bore defines a diameter adjacent the facing-away end of said second tubular member which is less than other portions of said second bore.

7. A wire-gripping handle.. for attaching to and detaching from catheter guidewires and the like, which handle comprises:
   a first tubular member having a first bore and a first side wall which defines a longitudinal slot extending along the entire length of and through both ends of said first tubular member, to permit a wire to be laterally inserted through said slot to occupy said first bore and to extend from said first bore longitudinally out of at least one end of said first tubular member;
   a second tubular member having a second bore which receives a portion of said first tubular member including said one end, whereby a wire extending out of said one end can also extend from said second bore out of the end of said second tubular member which faces away from said first tubular member, said second tubular member having a second side wall that defines a longitudinal, wire-passing slot extending between its ends;
   threaded means to permit said first and second tubular members to be rotatably advanceable and retractable relative to each other, the first tubular member and second bore being proportioned to radially collapse a portion of said first tubular member adjacent said one end as the first and second members are rotatably advanced relative to each other, to grip a wire carried therein, the one end of said first tubular member defining a plurality of radial slots to facilitate the radial collapse thereof.

8. The wire-gripping handle of claim 7 in which the one end of said first tubular member defines a substantially conical surface which, in turn, defines at least portions of said radial slots, said second tubular member defining a substantially conical step in the second bore adjacent the facing-away end of said second tubular member to fittingly engage said substantially conical surface, whereby pressurization between said surface and said step can cause said radial collapse.

9. The wire-gripping handle of claim 8 in which the portion of the first tubular member adjacent said one end has an outer diameter that is less than the other portions of said first tubular member.

10. The wire gripping handle of claim 9 in which the second bore defines a diameter adjacent the facing-away end of said second tubular member which is less than other portions of said second bore.

11. The wire-gripping handle of claim 7 in which the portion of the first tubular member adjacent said one end has an outer diameter that is less than the other portions of said first tubular member.

12. The wire gripping handle of claim 7 in which the second bore defines a diameter adjacent the facing-away end of said second tubular member which is less than other portions of said second bore.

* * * * *